United States Patent [19]

Nettelnstroth

[11] Patent Number: 5,382,153

[45] Date of Patent: Jan. 17, 1995

[54] APPARATUS FOR PRODUCING FILLING MATERIAL FOR THREE-DIMENSIONALLY SHAPED TEXTILE STRUCTURES

[75] Inventor: Karl Nettelnstroth, Augsburg, Germany

[73] Assignee: Hoechst Aktiengesellschaft, Germany

[21] Appl. No.: 748,675

[22] Filed: Aug. 22, 1991

[30] Foreign Application Priority Data

Aug. 25, 1990 [DE] Germany ............................ 4026916

[51] Int. Cl.⁶ ............................. B29B 9/06; B29B 9/14
[52] U.S. Cl. ....................................... 425/308; 156/166; 156/251; 156/441; 156/515; 264/103; 264/143; 264/345; 425/319; 425/391
[58] Field of Search ................ 264/103, 143, 140, 174, 264/109, 118, 122, 123, DIG. 47, DIG. 75, 345, 346; 156/441, 166, 515, 510, 518, 393, 251, 269; 425/302.1, 246, 319, 334, 391, 82.1

[56] References Cited

U.S. PATENT DOCUMENTS

| | | | |
|---|---|---|---|
| 2,349,829 | 5/1944 | Nydegger et al. | 425/302.1 |
| 2,438,156 | 3/1948 | Dodge | 156/515 |
| 2,451,597 | 10/1948 | Wheeler | 264/346 |
| 2,551,811 | 5/1951 | Mueller | 156/515 |
| 2,694,661 | 11/1954 | Meyer | 156/441 |
| 2,862,350 | 12/1958 | King et al. | 264/143 |
| 2,878,153 | 3/1959 | Hacklander | 264/257 |
| 2,948,649 | 8/1960 | Pancherz | 264/174 |
| 3,039,908 | 6/1962 | Parmele | 156/166 |
| 3,091,908 | 6/1963 | Carruthers | 57/2.5 |
| 3,095,343 | 6/1963 | Berger | 156/441 |
| 3,098,260 | 7/1963 | Richeson | 264/346 |
| 3,112,604 | 12/1963 | Davis | 156/441 |
| 3,120,690 | 2/1964 | Stevens | 156/441 |
| 3,327,461 | 6/1967 | Wyatt | 264/103 |
| 3,355,345 | 11/1967 | Braun | 156/515 |
| 3,364,289 | 1/1968 | Campbell | 264/103 |
| 3,501,562 | 3/1970 | Onoyama et al. | 264/103 |
| 3,516,380 | 3/1970 | Bittner et al. | 156/251 |
| 3,548,581 | 12/1970 | Bobkowicz | 264/103 |
| 3,656,383 | 4/1972 | Dibble et al. | 83/167 |
| 3,658,626 | 4/1972 | Berger et al. | 156/441 |
| 3,696,601 | 10/1972 | McCard | 57/285 |
| 3,703,429 | 11/1972 | Berger et al. | 156/441 |
| 3,730,813 | 5/1973 | Drummond | 156/441 |
| 3,883,718 | 5/1975 | Ferment et al. | 264/345 |
| 3,892,909 | 7/1975 | Miller | 428/371 |
| 3,943,028 | 3/1976 | Davis | 156/515 |
| 4,003,773 | 1/1977 | Grable | 264/143 |
| 4,100,013 | 7/1978 | Medler et al. | 156/441 |
| 4,115,495 | 9/1978 | Hartitz | 264/346 |
| 4,217,323 | 8/1980 | Foster et al. | 264/346 |
| 4,354,889 | 10/1982 | Berger | 156/441 |
| 4,378,725 | 4/1983 | Hospers et al. | 156/166 |
| 4,418,103 | 11/1983 | Tani et al. | 156/251 |
| 4,483,727 | 11/1984 | Eickman et al. | 156/251 |
| 4,707,977 | 11/1987 | Cousin et al. | 156/166 |
| 4,820,366 | 4/1989 | Beever et al. | 156/433 |
| 4,871,491 | 10/1989 | McMahon et al. | 264/29.2 |
| 4,892,018 | 1/1990 | Boggs | 83/15 |

Primary Examiner—Jay H. Woo
Assistant Examiner—Duane S. Smith
Attorney, Agent, or Firm—Connolly & Hutz

[57] ABSTRACT

Apparatus for producing filling material includes guide structure wherein a tow of filling and binding fiber is continuously guided through a heating zone in which the binding fiber becomes fused to the filling fiber at least at the surface of the tow, the tow is then continuously guided through a cooling zone in which at least a surface-consolidated tow is formed, and the consolidated tow is then continuously guided into a heated cutting means and cut and fused into tufts.

5 Claims, 4 Drawing Sheets

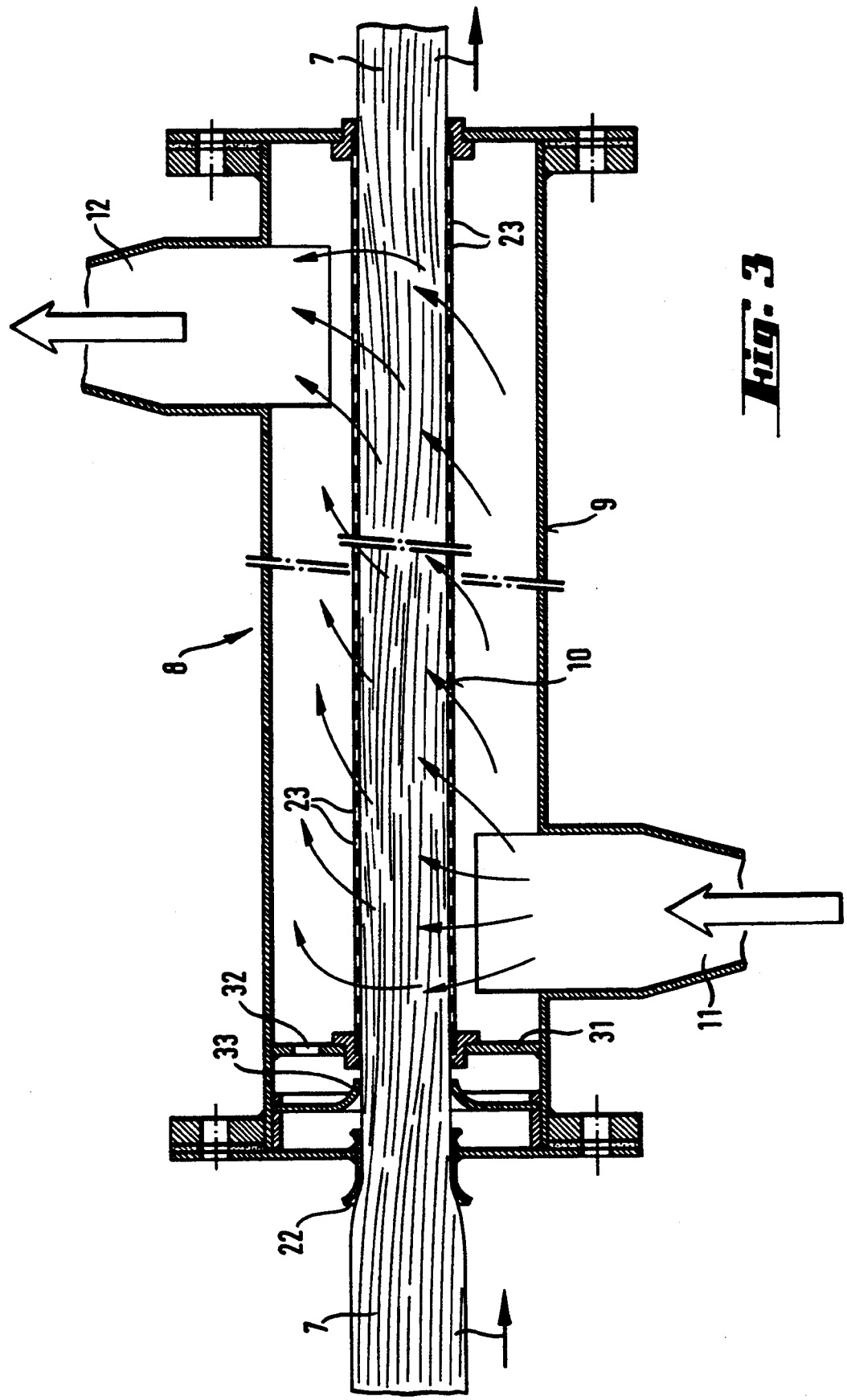

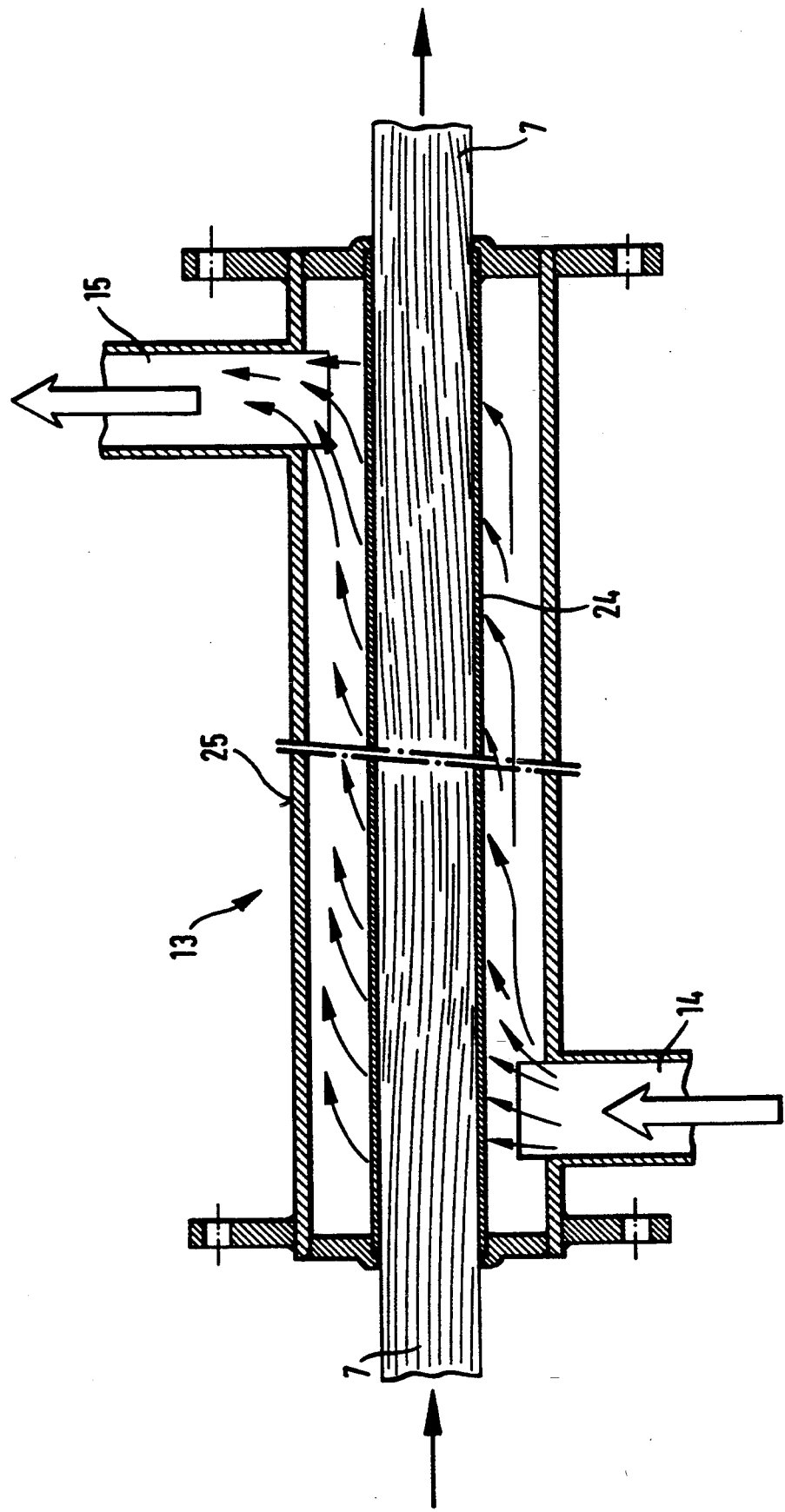

APPARATUS FOR PRODUCING FILLING MATERIAL FOR THREE-DIMENSIONALLY SHAPED TEXTILE STRUCTURES

BACKGROUND OF THE INVENTION

Process for producing filling material for three-dimensionally shaped textile structures and apparatus therefor The present invention relates to a novel production process for a textile filling material for three-dimensionally shaped textile structures and to an adapted apparatus for carrying out the process.

The filling material used for three-dimensionally shaped textile structures, for example pillows or bedding articles, is customarily feather and/or down and/or fiber. Filling fiber is generally incorporated in the form of card webs. These structures are mechanically not very stable, since the fibers adhere only loosely to one another. In use, therefore, these webs frequently disintegrate, forming clumps which can no longer be separated. Such card-consolidated filling webs based on bicomponent fibers are known from U.S. Pat. No. 3,589,956.

It is known to produce swabs of wadding from continuous lengths of wadding by consolidating a length of wadding comprising absorbent fibers and at least surface-fusible fibers by means of a heat treatment and subsequently stamping the swabs of wadding out of the consolidated length of wadding. For instance, DE-A-3,804,222 describes such a process, characterized in that the length of wadding is selectively heated, and subsequently cooled, in the areas to be stamped out, before the stamping out takes place. With the prior art processes appreciable loss of material as waste is likely, since with the stamping out of the length of wadding only parts thereof can be used directly. According to statements made in DE-A-3,804,222, the waste can amount to about 35–45% of the length of wadding.

SUMMARY OF THE INVENTION

There has now been found a process for producing filling material for three-dimensionally shaped textile structures where there is virtually no loss due to cutting out and whereby it is possible to produce a filling material which does not tend to clump and which can be fluffed up. Using the filling material produced by the process of the present invention it is possible to form a stabilized loft which can be preserved by plumping up even following prolonged use.

By "continuously guiding the fiber tow" and "continuously feeding into a cutting means" the fiber tow moves without interruption at least between the heating zone and the cutting means.

The various zones in the process of the present invention can be arranged horizontally or else vertically. In the case of a vertical arrangement, the feed zone can be situated at the upper or else at the lower part of the apparatus. If it is situated in the upper part of the apparatus, the fiber tow to be processed is first guided upward and introduced into the feed zone and then moves downward through the heating and cooling zones toward the cutting zone. If the feed zone is situated in the lower part of the apparatus, the fiber tow to be processed moves upward through the heating and cooling zones toward the cutting zone.

In the process of the present invention it is possible to use virtually any fiber tow, as long as it consists of a combination of filling fibers and binding fibers. And this fiber tow may comprise continuous filament fiber or in particular staple fiber. A staple fiber tow may be produced in any desired manner. It can be for example a stretch-broken or a card sliver, e.g. a flat card sliver or a roller-and-clearer card sliver. The fibers or filaments forming the tow customarily have a crimp, preferably a two- or three-dimensional crimp. The linear density of the tow is advantageously about 1 to 12 ktex, preferably 4 to 12 ktex, in particular 6 to 8 ktex. The linear density of the tow is determined inter alia by the dimensions of the processing range, for example by the capacity of the transport means and/or by the dimensions of the heating or cooling zone. There is thus no reason why a tow having a linear density different from that mentioned above should not be used.

The linear density of the staple or filament fiber forming the tow is customarily between 2 and 15 dtex preferably between 4 and 7 dtex. It is also possible to use mixtures of linear densities. The linear densities of the filling fibers and the binding fibers are chosen in such a way that, for a given heat output in the heating zone and for a given transport speed of the tow through this zone, the two types of fiber can become fused to one another at least at the surface of the tow to such an extent that adequate consolidation for the end use in mind can be obtained in the subsequent cooling zone.

The filling-fiber portion of the tow can in principle be any textile fiber suitable for this purpose. Such a fiber can be a natural fiber, for example cotton or wool, or it can be a man-made fiber, in particular a synthetic fiber, for example a polyamide, polyester or polyacrylonitrile fiber. The preferred filling fiber is polyester fiber, in particular fiber based on polyethylene terephthalate.

The binding-fiber portion of the tow can in principle be any fiber made of a thermoplastic material, although if the filling fibers are thermoplastic it is necessary to use binding fiber having a lower softening point than the filling fiber, preferably binding fiber having a softening point which is 10° C., in particular 30° C., lower than that of the thermoplastic filling fiber. The preferred binding fiber used is fiber made of thermoplastic polyester, preferably fiber based on polyethylene terephthalate, in particular modified polyethylene terephthalate. Very particular preference is given to using binding fiber comprising polyester bicomponent fiber with a core/sheath structure, in which the sheath is in particular constituted by a copolyester which has a lower softening point than the polyester which forms the core. However, it is also possible to use bicomponent fibers which consist of different polymers, for example a polyester core and a sheath made of a lower-melting polymer, for example a polyolefin. Examples of suitable bicomponent fibers are described in U.S. Pat. No. 3,589,956.

The filling fibers can be combined with the binding fibers even as the tow is being formed; or tows, in particular card slivers made of different fiber types are combined with one another upstream of and fed together into the heating zone. This combining can take the form of simply gathering the tows together or of doubling tows of different fibers. The proportion of filling fiber in the tow is about 50–95% by weight, based on the amount of filling and binding fiber, and the proportion of binding fiber is accordingly 50–5% by weight. Preferably, the proportion of filling fiber is about 75% by weight and the binding fiber about 25% by weight.

The temperature in the heating zone must be chosen in such a way that the binding fibers become fused to the filling fibers at least at the surface of the tow, so that the tow becomes consolidated in the subsequent cooling zone to such an extent as to be sufficiently stable for use as a filling material. Of course, in the heating zone the binding fibers can be melted throughout the entire cross-section of the tow.

The heating can be effected in any desired manner, for example by irradiation or by contact with hot fluids or with heated guide elements for the tow. For instance, the tow can be passed through a heating zone in which infrared radiation or microwave radiation acts on the tow or in which a heated fluid, in particular heated air, is squeezed and/or sucked through the tow or passed over the surface of the tow, or the tow is passed through a hot pipe and is melted at least at the surface as the result of contact with the hot inner surface of the pipe.

In the cooling zone, the heated tow is transported either through a cooling apparatus or cooled down with the aid of the ambient temperature. At any rate, the tow must be cooled down in this zone to such an extent that it is sufficiently solid for the subsequent cutting operation and does not disintegrate into individual fibers on cutting.

If a cooling apparatus is used, suitable coolants are in particular cooled fluids, in particular cooled air, which are squeezed and/or sucked through the tow or passed over the surface of the tow, or the tow is passed through a pipe and is cooled down at least at the surface as a result of contact with the cooled inner surface of this pipe to such an extent that the desired consolidation is obtained.

The consolidated tow can be cut with any cutting device known for tows. Examples thereof are cutting wheels with fixed blades on the outside, onto which the consolidated tow is wound until the winding pressure on the inside coils of the tow has increased to such an extent that the blades cut through these inner coils. The tow can also be guided past a bladed head whose blades rotate perpendicularly to the transport direction of the tow and cut it.

Preferably, the tow is guided with contact pressure underneath or over a rotating cutter wheel so that the tow need not be wound up. Very particular preference is given to using cutting means comprising heated blades, so that the plane of section being formed during the cutting process is at a temperature such that the binding fibers become fused to the filling fibers at least at the surface of the plane of section being formed, so that the result is the formation of an essentially smooth surface which has virtually no free fiber ends. In this way it is possible to produce rectangular or square tufts of fiber.

The tow is transported through the various processing zones by transport means customary for this purpose, such as dies through which the tow is conveyed by means of a transport medium or, in particular, pairs of rollers which support and transport the tow at one or more places of the apparatus. Preferably, such transport rollers are situated between the cooling zone and the cutting means. In a pair of rollers, one roller can perform a transport function while the other roller presses the tow against the transport roller.

The invention also provides an apparatus for carrying out the above process.

BRIEF DESCRIPTION OF THE DRAWING

In what follows, the process and the suitable apparatus therefor are described by way of example with reference to drawings, of which FIG. 3 is a longitudinal section through a heating means of the process of the invention, and FIG. 4 is a longitudinal section through a cooling means of the apparatus of the invention.

DETAILED DESCRIPTION THE INVENTION

Figure 1:
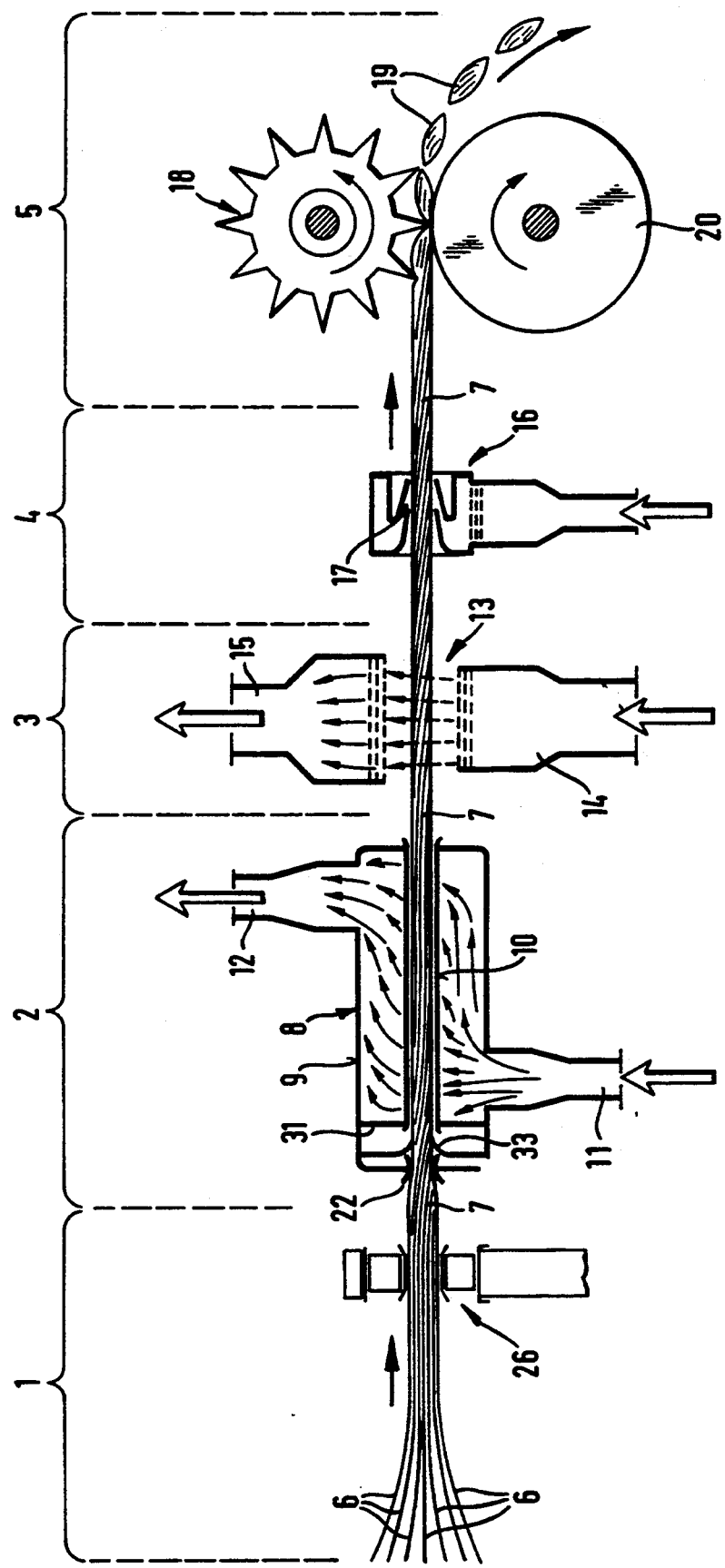
FIG. 1 is a schematic side view of an apparatus for processing a card sliver by the process of the invention.

In FIG. 1 an embodiment of the claimed process is shown in a schematic representation. The sliver (6) from a carding machine passes via a feed zone (1) into a heating zone (2) which is followed by a cooling zone (3), a transport zone (4) and a cutting zone (5). The card sliver (6) is additionally mechanically stabilized before entry into the heating means (8) by being false-twisted by means of the device (26). This operation is not absolutely necessary, but it is preferable, especially in the case of card slivers. Stabilization may be effected in a conventional manner, for example by false-twisting the card sliver (6) using air or mechanical friction, for example rubbing.

After the false twist has been applied, the mechanically consolidated fiber tow (7) is introduced into a heating means (8). In FIG. 1 this heating means is shown as a jacket heater within which the tow (7) passes through a tube (10). This tube (10) is surrounded by a heating jacket (9) through which a fluid flows, entering via the intake port (11) and leaving via the exit port (12). The inlet port (11) and the exit port (12) can also be arranged the other way round. The tube (10) can be surrounded by the stream of fluid, so that the tow (7) is heated, as depicted, through contact with the hot tube walls, or the tube (10) can have openings, so that the fluid itself can come into contact with the tow (7). Preferably, the fluid used is hot air, and it is made to act directly on the tow (7) by means of a perforated tube (10) (not depicted here; cf. FIG. 3). By using a narrower tube diameter the tow (7) can be additionally compacted. To this end, the entry of the tow (7) into the tube (10) is facilitated by dies (22) and (33). The heating zone (2) is followed by the cooling zone (3). In the embodiment of FIG. 1, this cooling zone is represented as a cooling apparatus (13). It serves to bring a coolant fluid, preferably air, into contact with the fiber tow either directly or via a cooling surface (not depicted). The fluid can flow cocurrently with or countercurrently to the tow transport direction or preferably, as depicted, perpendicularly thereto. In FIG. 1 the fluid is introduced via the inlet port (14), forced through the tow (7) and discharged via the exit port (15). The cooled, consolidated tow (7) is then passed toward a transport means (16) which in the form depicted in FIG. 1 is an annular die (17) within which the tow (7) is moved by means of a fluid, preferably air. After passing through the transport zone (4) the consolidated tow is passed toward a cutting zone (5) within which a cutting wheel (18) cuts it into tufts (19). The tow (7) is pressed against the cutting wheel (18) by a pressure roll (20).

Figure 2:
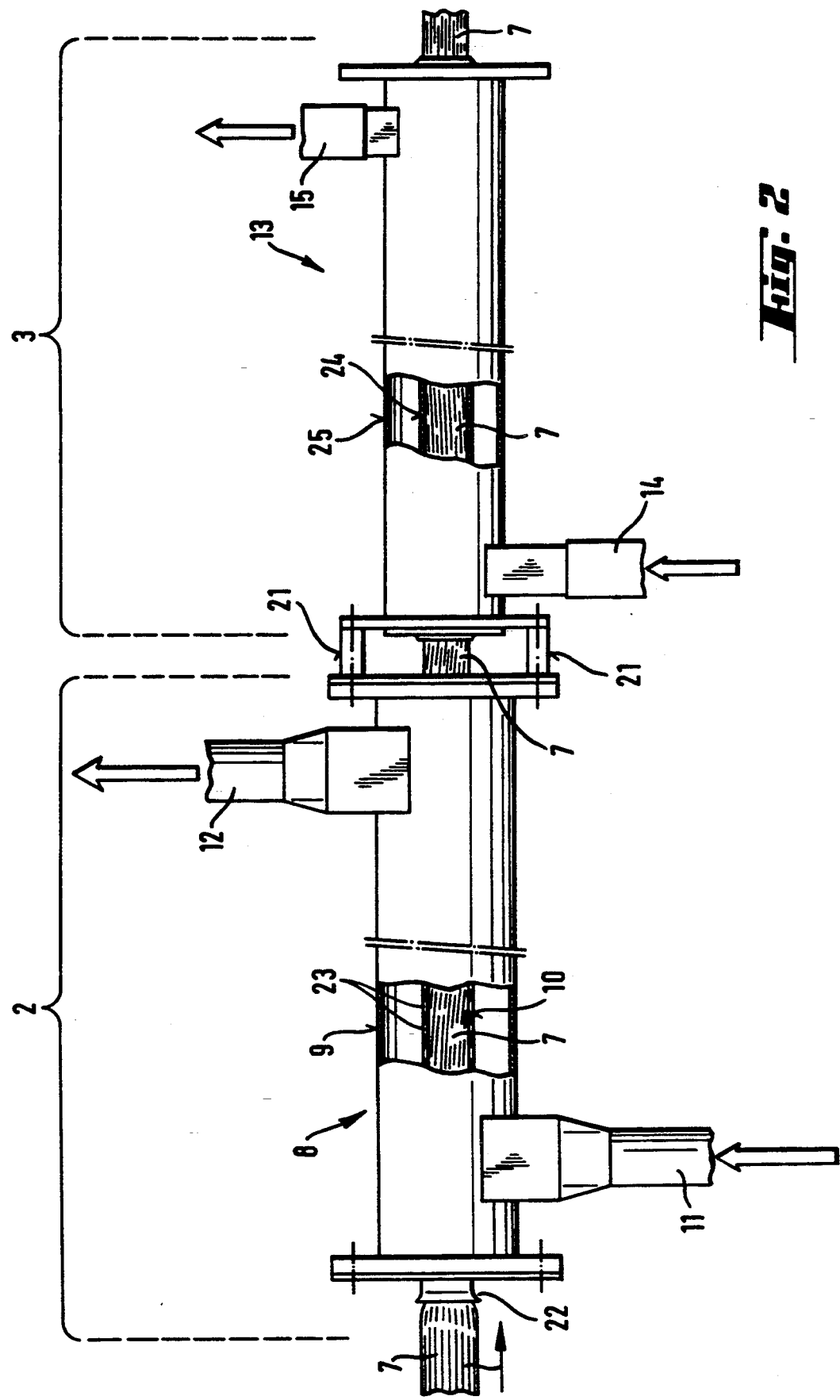
FIG. 2 is a side view of an embodiment of the heating and cooling means of the apparatus of the invention.

FIG. 2 shows a particular embodiment of the heating zone (2) and the cooling zone (3). The heating means (8) is here likewise constructed as a jacket heater. The heating jacket (9) is supplied with the heating fluid via the inlet port (11) and the exit port (12). The fiber tow (7) passes through the inlet die (22) into the guiding tube (10), preferably arriving at that point in a compacted form. The heating means (8) is connected via spacer bushes (21) directly to the cooling apparatus (13), which is surrounded by a cooling jacket (25). The coolant is fed into the cooling jacket via the inlet port (14) and discharged via the exit port (15).

FIG. 3 shows a particular embodiment of the heating means (8). In this embodiment, the tube (10) has been provided with holes (23), so that the fluid passing through the jacket (9) can flow through the tube (10) and the tow (7) being guided therein. The tube (10) preferably has holes along its entire length. However, it is also possible to conceive of embodiments in which the tube (10) is perforated only over part of its length. The support (31) for the guide tube (10) has been provided with openings (32) for the heating fluid. The funnel-like shape of the inlet (33) further improves the entry of the fiber tow (7).

FIG. 4 shows the cooling apparatus (13) in more detail and in section. On the inside is a tube (24) into which the tow (7) is guided. This tube (24) can have perforations in the same way as the heating means. However, in the case of liquid cooling media the tube (24) is preferably unbroken, in which case the cooling medium acts only indirectly on the tow (7) via the tube walls. The tube (24) is surrounded by the jacket (25) which is supplied with the coolant via the inlet port (14) and the exit port (15), which ports (14) and (15) can also be arranged the other way round.

The following Example illustrates the invention without limiting it:

Blends of polyethylene terephthalate and bicomponent fibers based on polyethylene terephthalate and modified polyethylene terephthalate (core/sheath fibers) are processed on carding machines to form slivers. The filling fibers used are TREVIRA® 290 (staple fiber 6.7 dtex/60 mm) or TREVIRA® 206 (staple fiber 6.0 dtex/60 mm) and the binding fibers used are TREVIRA® 252 (staple fiber 3.0 dtex/50 mm), in a blend of 75% by weight filling fiber and 25% by weight binding fiber. The slivers are consolidated by heating at a temperature of about 180° C. The thermally treated material is then immediately cooled and preferably formed. The formed and consolidated slivers are then cut into various lengths, preferably 2-6 cm, and blown into bedding articles, such as pillows. The material does not tend to clump, and pillows filled therewith can be plumped up without causing the tufts to disintegrate or become interlinked.

What is claimed is:

1. Apparatus for producing filling material from a tow of continuous filament or staple fiber containing at least one kind of filling fiber and at least one kind of binding fiber comprising
a production line including a feed zone, heating means downstream of the feed zone, cooling means downstream of the heating means, and heated tow cutting means comprising a plurality of spaced apart heated cutter blades downstreams of the cooling means for cutting the tow into pieces while fusing the binding fibers to the filling fibers where tow is cut, guide structure for continuously guiding the tow from the feed zone through the heating and cooling means into and through the heated tow cutting means, and annular die located between the cooling means and the heated tow cutting means for transporting the tow via a fluid means along the guide structure.

2. Apparatus as in claim 1 wherein the feed zone includes structure constructed and arranged for applying a false twist to the tow.

3. Apparatus as in claim 1 wherein the heating means comprises a jacketed heater having inlet and outlet lines for a heating medium, and a perforated guide tube within the jacketed heater through which the tow travels, the perforated guide tube having a diameter smaller than the entering tow whereby the tow is compacted and mechanically stabilized within the guide tube.

4. Apparatus as in claim 1 wherein the cooling means comprises a jacketed cooler having inlet and outlet lines for a cooling medium, and an imperforate guide tube within the jacketed cooler through which the tow travels.

5. Apparatus as in claim 4 wherein the cooling medium is water.

* * * * *